United States Patent [19]

Lipton

[11] Patent Number: 5,455,279
[45] Date of Patent: Oct. 3, 1995

[54] REGIMEN METHOD OF MEDIATING NEURONAL DAMAGE USING NITROGLYCERINE

[75] Inventor: Stuart A. Lipton, Newton, Mass.

[73] Assignee: The Children's Medical Center Corporation, Boston, Mass.

[21] Appl. No.: 25,028

[22] Filed: Mar. 2, 1993

Related U.S. Application Data

[63] Continuation-in-part of Ser. No. 949,342, Sep. 22, 1992, Pat. No. 5,234,956, which is a continuation of Ser. No. 688,965, Apr. 19, 1991, abandoned.

[51] Int. Cl.[6] .................. A61K 31/13; A61K 31/045; A61K 31/04
[52] U.S. Cl. ........................ 514/742; 514/724
[58] Field of Search ........................ 514/724, 668, 514/742

[56] References Cited

U.S. PATENT DOCUMENTS

| | | | |
|---|---|---|---|
| 4,513,137 | 4/1985 | Koser et al. | 546/14 |
| 4,806,543 | 2/1989 | Choi | 514/464 |
| 5,091,391 | 2/1992 | Aizenman et al. | 514/311 |

FOREIGN PATENT DOCUMENTS

WO91/02810  8/1990  WIPO .

OTHER PUBLICATIONS

*Choi, Neuron 1:623 (1988).
Rothman et al., Trends in Neurosci. 10:299 (1987).
Meldrum et al., Trends in Pharm. Sci. 11:379–387 (1990).
Weiss et al., Science 247:1474 (1990).
Garthwaite et al., Trends in Neurosci. 14:60–67 (1991).
Hope et al., Proc. Natl. Acad. Sci. USA 88:2811–2814 (1991).
Aizenman et al., Neuron 5:8411–(1990).
Majewska et al., Brain Res. 537:328–332 (1990).
Levy et al., Neurosci. Letters 110:291–296 (1990).
Sucher et al., Neuropharmacology and Neurotoxicity 1:29–32 (1990).
Seubert, Brain Research 492:366–370 (1990).
Sernagor, Neuron 2:1221–1227 (1989).
Goldberg et al., J. Pharm. Exp. Therapeutics 245:1081–1087 (1988).
Davenport et al., Eur. J. Pharm. 154:73–78 (1988).
Choi et al., J. Pharmacol. and Exp. Therapeutics 242:713–720 (1987).
Garthwaite et al., Neuroscience 26:321–326 (1988).
Merck Index, 9th Edition, pp. 858–859 #6429 (1976).
Majewska et al., Society For Neuroscience Abstracts, vol. 15, p. 1167, No. 463.15 (1989).
Aizenman et al., Neuron 2:1257–1263 (1989).
Choi, Neuron 1:623–634 (1988).
Lipton et al., "A redox–based mechanism for the neuroprotective and neurodestructive effects of nitric oxide and related nitroso–compounds," Nature, 364:626–632, 1993.
Stamler, "Biochemistry of Nitric Oxide and Its Redox–Activated Forms," Science, 258:1898–1902, 1992.
Lipton and Stamler, "Action of Redox–Related Congeners of Nitric Oxide at the NMDA Receptor", Neuropharmacology, 33:1229–1233, 1994.
Stueher et al., FASEB J. 5:98–103, 1991.
Lei et al., Neuron 8:1087–1099, 1992.
Gallop et al., "Is the antioxidant, anti–inflammatory putative new vitamin, PQQ, involved with nitric oxide in bone metabolism?", Connective Tissue Research 29:153–161, 1993.
Beckman, J., "The double–edged role of nitric oxide in brain function and superoxide–mediated injury," J. Dev. Physio. 15:53–59 1991.
Beckman, et al., "Apparent hydroxl radical production by peroxynitrite: Implications for endothelial injury from nitric oxide and superoxide," Proc. Nat'l Acad. Sci. USA 87:1620–1624, 1990.
Cross, et al., "The effect of the inhibitor diphenylene iodonium on the superoxide–generating system of neutrophils", Biochem. J. 237:111–116 1986.
Dawson, et al., "Mechanisms of nitric oxide–mediated neurotoxicity in primary brain cultures," J. Neurosci. 13:2651–2661, 1993.
Holland, et al., "Mechanism of Action of the Hypoglycemic Agent Diphenyleneiodonium," J. Biol. Chem. 248:6050–6056, 1973.
Huang, et al., "Effects of Cerebral Ischemia in Mice Deficient in Neuronal Nitric Oxide Synthase", Science 265:1883–1885, 1994.
Ignarro, L., "Nitric Oxide: A novel signal transduction mechanism for transcelluar communication," Hypertension 16:477–483, 1990.

Primary Examiner—Marianne M. Cintins
Assistant Examiner—T. J. Criares
Attorney, Agent, or Firm—Fish & Richardson

[57] ABSTRACT

Disclosed is a method for decreasing NMDA receptor-mediated neuronal damage in a mammal by administering to the mammal a nitroso-compound that generates nitric-oxide or related redox species, in a concentration effective to effect neuroprotection. Also disclosed is a method for decreasing NMDA receptor-mediated neuronal damage in a mammal by administering to the mammal a nitroso-compound that generates nitric oxide (or a related redox species such as $NO^{31}$ or $NO^+$equivalent), or a physiologically concentration effective to cause such neuroprotection.

11 Claims, 7 Drawing Sheets

REGIMEN METHOD OF MEDIATING NEURONAL DAMAGE USING NITROGLYCERINE

BACKGROUND OF THE INVENTION

This application is a continuation-in-part of my earlier application U.S. Ser. No. 07/949,342, filed Sep. 22, 1992, now U.S. Pat. No. 5,234,956 which in turn is a continuation of U.S. Ser. No. 07/688,965, filed Apr. 19, 1991, now abandoned. See also Lipton, PCT WO91/02180. Each of the above applications is hereby incorporated by reference.

This invention relates to the treatment of nervous system disorders, particularly disorders mediated by the N-methyl-D-aspartate (NMDA) subtype of excitatory amino acid receptor complex.

Glutamate or related congenors have been implicated as a significant factor in the neurotoxicity associated with hypoxic-ischemic encephalopathy, anoxia, hypoglycemia, seizures, trauma, and several degenerative neurological disorders (Hahn et al., *Proc. Natl. Acad. Sci. USA* 85:6556, 1988; Choi, *Neuron* 1:623, 1988; Rothman et al., *Trends Neurosci.* 10:299, 1987; Meldrum et al., *Trends Pharm. Sci.* 11:379, 1990). In many central neurons the predominant form of this neurotoxicity appears to be mediated by activation of the NMDA subtype of glutamate receptor and subsequent influx of excessive $Ca^{2+}$ (Choi, ibid; Weiss et al., *Science* 247:1474, 1990). Lei et al. Neuron 8:1087–1099 (1992) discloses the use of nitroso-compounds (compounds containing the NO group) to treat neurological diseases. Stamler et al. *Science* 258:1898–1902 (1992) by referencing Lei et al. (1992) also discloses the use of nitroso-compounds to treat neurological diseases.

SUMMARY OF THE INVENTION

I have discovered that certain compounds protect neurons against NMDA receptor-mediated neuronal damage. Specifically, nitroglycerin, nitroprusside, and their nitroso-compound derivatives provide such protection. Thus, one aspect of the invention features a method for decreasing NMDA receptor complex-mediated neuronal damage in a mammal by administering one of the above-described compounds to the mammal, in a concentration effective to decrease such damage.

With regard to the compounds of the first aspect of the invention, I do not wish to bind myself to any particular theory or mechanism of action. However, it appears that oxidation of the thiol group(s) of the NMDA receptor's redox modulatory site protect against NMDA receptor-mediated neuronal damage. It is also known that the active species of nitroglycerin and nitroprusside is nitric oxide or related NO redox species.[1] See, e.g., Garthwaite et al. (*Trends in Neurosciences* 14:60, (1991). One possible mechanism for the protective effect that I have discovered is NO-induced oxidation of the NMDA receptor-channel complex, probably mediated by a nitrosation reaction involving transfer of the NO group to the thiol(s) of the NMDA receptor's redox modulatory site, resulting in an RS-NO ($NO^+$ equivalent). Similarly, the redox species nitroxyl anion ($NO^-$) can also react with thiol groups. In contrast, under physiological conditions, NO. (nitric oxide) reacts directly with thiol groups poorly, if at all.

[1] I use the term NO (nitrogen monoxide) to include the related redox species, i.e., NO. (nitric oxide), $NO^+$ (nitrosonium 25 ion), and $NO^{31}$ (nitroxyl anion). See Stamler et al., cited above.

A second aspect of the invention features a method for decreasing NMDA receptor complex-mediated neuronal damage by administering a nitroso-compound, in a concentration effective to cause neuroprotection— e.g., a decrease in such damage. Without wishing to bind myself to a specific mechanism of action, it appears that NO or a related redox species acts on the thiol group(s) of the redox modulatory site of the NMDA receptor-channel complex to protect against NMDA receptor-mediated damage.

In preferred embodiments of both aspects of the invention, the mammal is a human patient infected with a virus affecting the nervous system—e.g., measles or human immunodeficiency virus (HIV). In particular, the patient being treated may be infected with HIV and may manifest symptoms of the AIDS related complex or acquired immunodeficiency syndrome (for example neurological manifestations of HIV (see, e.g., U.S. Ser. No. 571,949), such as those that may be treated according to the present invention, including, but not limited to, AIDS dimentia complex or cognitive-motor-sensory deficits of incipient or progressing dementia). Other neuro-degenerative states that can be treated according to the invention include Alzheimer's disease, Huntington's disease, amyotrophic lateral sclerosis (ALS or motor neuron disease), Parkinson's disease, neurolathyrism, Guam disease, and those listed in table 2, below. Alternatively, the patient may have (or be likely to be subject to) an acute disorder such as hypoxia, anoxia, carbon monoxide poisoning, ischemia, CNS trauma, hypoglycemia, seizures, stroke (by which I mean to include stroke associated with ischemia or subarachnoid hemorrhage), domoic acid poisoning, lead poisoning, or other acute disorders listed on Table 1, below. Where the patient is likely to be subject to one of the above conditions, the patient could be treated prophylactically according to the invention. Other diseases mediated (at least in part) by excitatory amino acid toxicity and can be treated by NMDA receptor complex modulation according to the present invention. Such diseases include: 1) ALS (amyotrophic lateral sclerosis or motor neuron disease); 2) painful types of "peripheral neuropathy" which may be mediated by excessive glutamate (NMDA) receptor stimulation, e.g., causalgia and other types of neuropathic pain syndromes, including painful types of peripheral neuropathy which may (but need not necessarily) include a central nervous system component.

By "NMDA receptor-mediated neuronal damage" is meant any neuronal injury which is associated with stimulation or co-stimulation of the NMDA receptor-channel complex, a receptor-channel complex which is found on a subset of mammalian neurons and which includes a binding site for a molecule such as glutamate, NMDA, or similar agonists (see below). Activation of this receptor-channel complex by binding agonists induces neuronal excitation by opening specific ion channels in the membrane.

By a "nitroso-compound" is meant any compound which produces a sufficient amount of NO (most probably a related redox species such as an $NO^+$ or $NO^-$ equivalent) upon administration to a mammal to decrease neuronal damage or injury. For convenience, I have also used the less precise term "NO-generating compound" to include compounds that produce the above described NO-related redox species (e.g., RS-NO, an $NO^+$ equivalent, or $NO^-$) or a physiologically acceptable salt thereof.

Useful compounds of the second aspect of the invention include any nitroso-compound. Verification that a particular compound provides protective oxidation of the NMDA receptor itself is a step well understood by those skilled in the art (see, e.g., Lipton, PCT WO 91/02810).

The two preferred compounds of the first aspect of the invention (i.e., nitroglycerin and sodium nitroprusside) provide the advantage of a proven record of safe human administration (i.e., for treatment for cardiovascular disorders). Other nitroso-compounds that can be used in the method of the invention include: isosorbide dinitrate (isordil); S-nitroso captopril (Snocap); Serum albumin coupled to nitric oxide ("SA-NO"); Cathepsin coupled to nitric oxide (cathepsin - NO); tissue plasminogen activator coupled to NO (TPA-NO); SIN-1 (or molsidomine) cation-nitrosyl complexes, including $Fe^{2+}$-nitrosyl complexes; Nicorandil; S-nitrosoglutathione; NO coupled to an adamantine derivative, including memantine (see U.S. patent application Ser. No. 07/934,824 hereby incorporated by reference); S-nitrosothiols including S-nitrosocysteine; quinones, including pyrroloquinoline quinone (PQQ), ester derivatives of PQQ, or ubiquinone; sydnonimins or nonoates having the formula

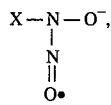

where X is any nucleophile including an amine; and agents which generate an oxidizing cascade similar to that generated by $NO^2$ such as e-lipoic acid (thioctic acid and its enantiomers); dihydrolipoate; glutathione; ascorbate; and vitamin E.

[2] Without wishing to be bound to a specific theory, such cascades are characterized by electron exchange with nitroso-compounds.

Any of the above described nitroso-compounds may be combined with other redox compounds that facilitate production and maintenance of NO. For example, direct NO-generators can be combined with pyroloquinoline quinone (PQQ), a known NMDA redox modulator (see U.S. Pat. No. 5,091,391), or PQQ's derivative esters, or other quinones such as ubiquinone.

Regarding compounds according to the second aspect of the invention, the ability of NO to be transported to and cross cell membranes facilitates therapies according to the invention.

A third aspect of the invention is based on the recognition that the redox species NO, (nitric oxide containing one free electron) leads to neurotoxicity via formation of peroxynitrite ($ONOO^-$) (or its decomposition products) by reaction with $O_2.^-$ (see FIG. 7, below for demonstration). Applicant notes that the literature describes the enzyme, NO synthase, which produces nitric oxide in certain cell types; this enzyme and its role in neuronal function is discussed in, e.g., Garthwaite et al. (*Trends in Neurosciences* 14:60, 1991), Hope et al. (*Proc. Natl. Acad. Sci. USA* 88:2811, 1991), and Dawson et al., (*Ann. Neurol.* 32:297–311, 1992). According to this third aspect of the invention, nitric oxide synthase is inhibited to effect neuroprotection. This aspect of the invention features administering inhibitors of nitric oxide sythase to decrease the availability of NO. and hence decrease the availability of neurotoxic peroxynitrite ($ONOO^-$). This aspect of the invention may be combined with the first two aspects of the invention or the nitric oxide syntase inhibitor may be administered independently to treat neurological manifestations of infection with an HIV, to treat neuropathic pain mediated by NMDA teceptor activity, or to treat ALS.

A fourth aspect of the invention features the recognition that neuroprotective dosages of nitrosocompounds can lower blood pressure as an undesirable side effect in naive patients, but that it is possible to build tolerance to this side effect without losing the desired neuroprotective effect.

Accordingly, the fourth aspect features administering a nitroso compound capable of protecting against NMDA receptor complex-mediated neuronal injury, continuously over an extended period with gradually escalating dosage, beginning at a dosage level which does not substantially reduce the patient's blood pressure, and increasing to a later dosage level to systemic tolerance of the compound. The later dosage level is high enough to substantially reduce a naive patient's blood pressure, but the continuous administration of the compound builds tolerance to the compound's blood-pressure lowering effect, so that the later dosage level does not in fact substantially reduce the patient's blood pressure.

Nitroglycerin is the preferred compound for the fourth aspect of the invention. It may be administered by transdermal patch as described in detail below (e.g. a patch having a surface area over 50 cm$^2$). Preferably such administration is continous over a period exceeding 24 hours.

It is also useful, when acutely administering a nitroso compound according to the first two aspects of the invention, to co-administer a blood-pressure increasing compound such as dopamine.

A fifth aspect of the invention features the administration of superoxide dismutase (SOD), catalase, or both, to limit neurotoxicity by decreasing the formation of peroxynitrite from the reaction of NO. with superoxide anion ($O^2.^-$). The treatment can be adjunctive with the first two aspects of the invention or it can be used independently, particularly to treat neurological manifestations of infection with HIV or of ALS. Polyethylene glycol (PEG) is used to enhance absorption into the central nervous system (CNS) and efficacy of SOD and/or catalase. An SOD mimic, the protein-bound polysaccharide of Coriolus versicolor QUEL, termed "PS-K", may also be effective by parenteral or oral routes of administration, especially with PEG to enhance CNS absorption, and such mimics may be substituted for SOD in this aspect of the invention. See Kariya et al., *Mol. Biother.* 4:40–46 (1992); and Liu et al., (1989) *Am. J. Physiol.* 256:589–593.

Other features and advantages of the invention will be apparent from the following detailed description and from the claims.

DETAILED DESCRIPTION

The drawings are first briefly described.

Figure 1:
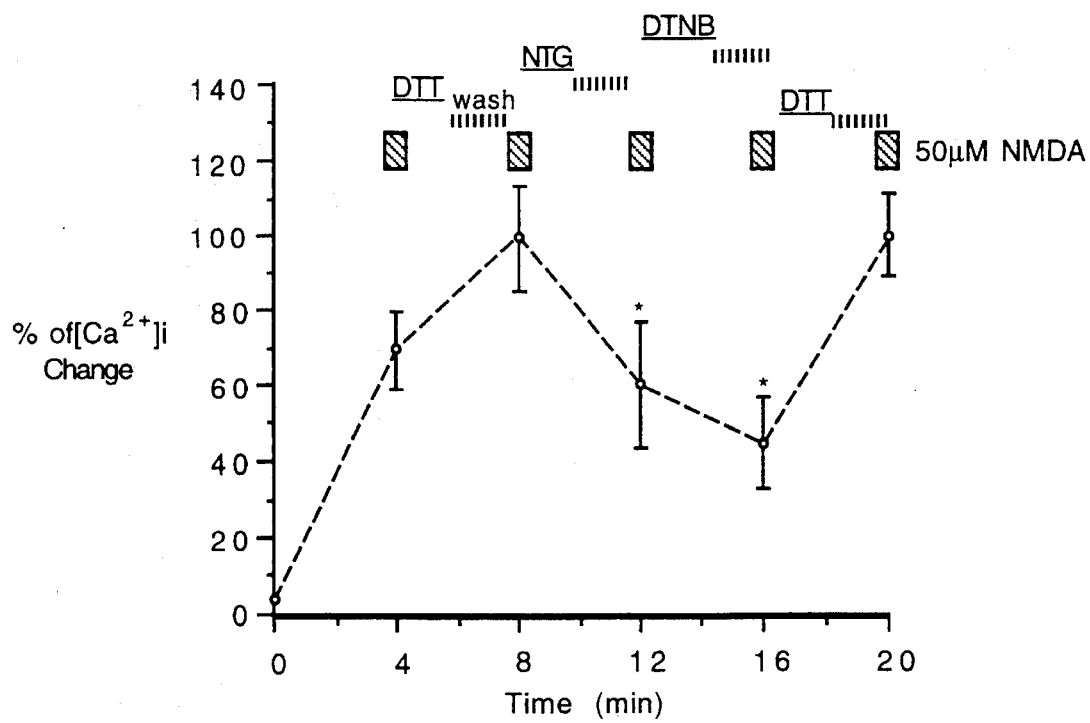
Figure 2:
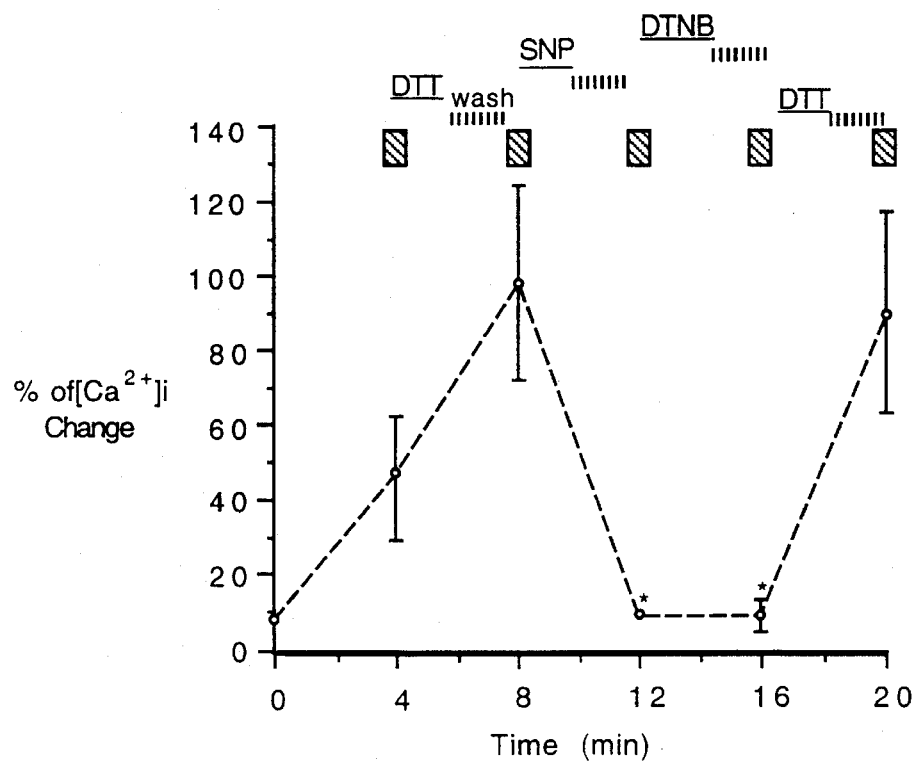
Figure 3:
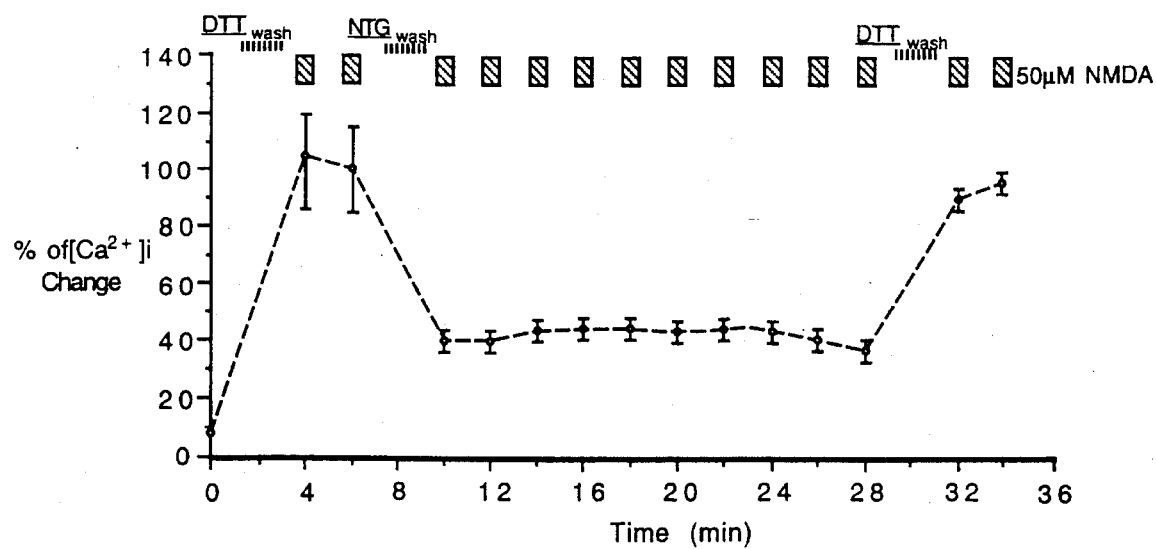

Drawings FIGS. 1–3 are graphs showing NMDA-evoked intracellular [Ca$^{2+}$] levels observed by fura-2 imaging over time as different redox agents including NTG are administered to cultured neurons. (See Examples 1 and 2.)

Figure 4:
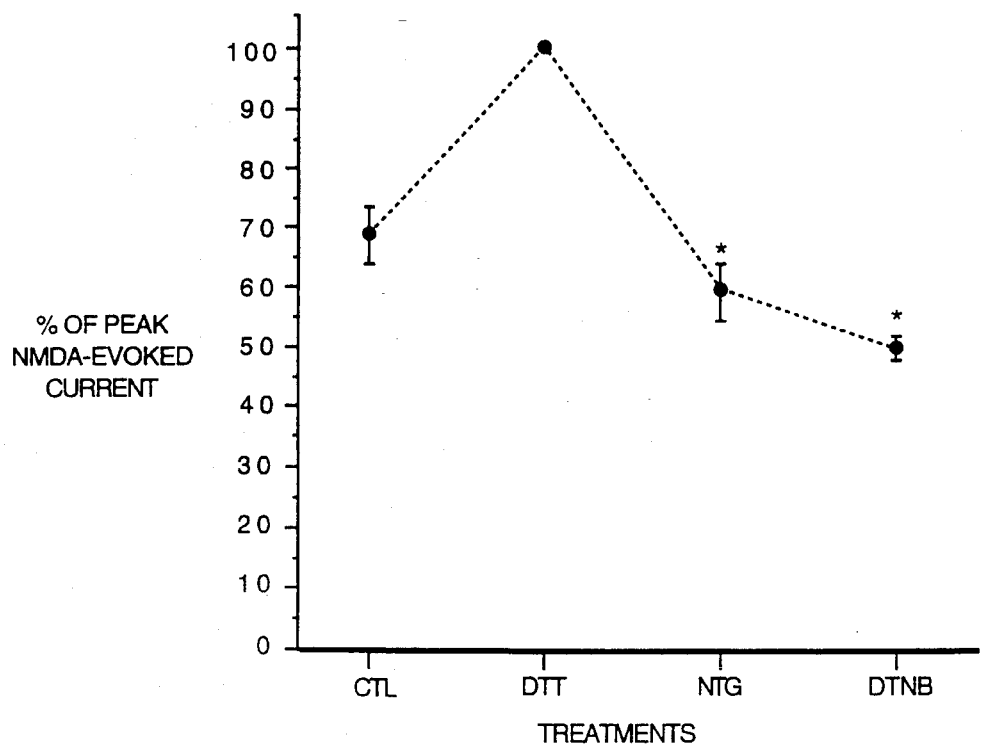

FIG. 4 is a graph showing NMDA-evoked currents (including [Ca$^2$+]) in cortical neurons and the effect of different redox agents including NTG. (See Example 3.)

Figure 5A:
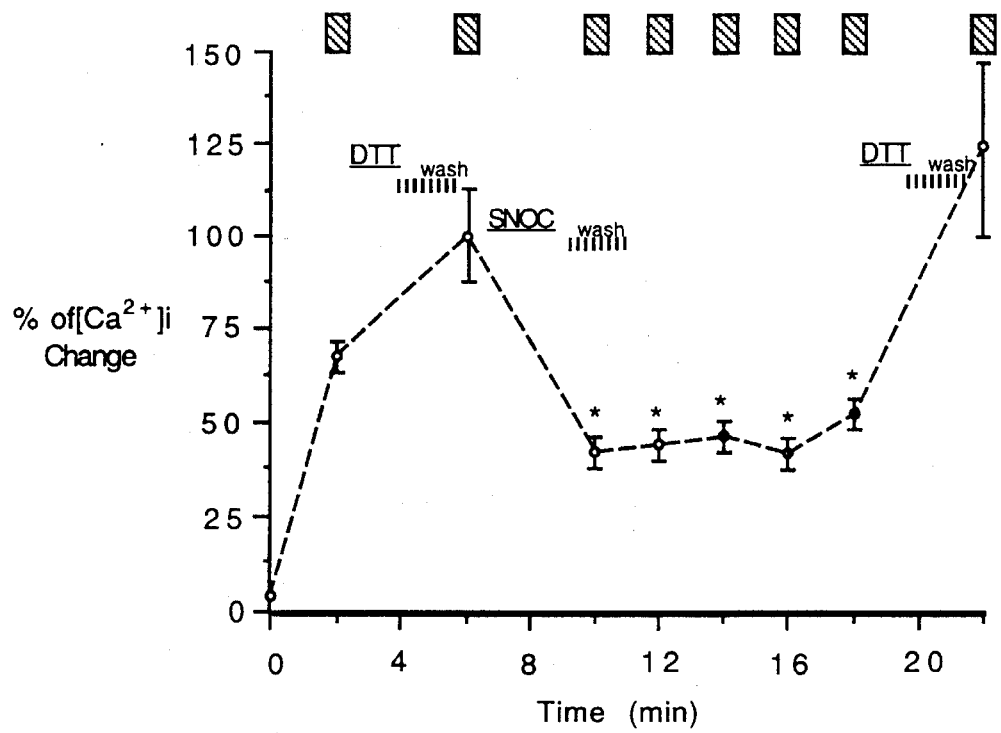
Figure 5B:
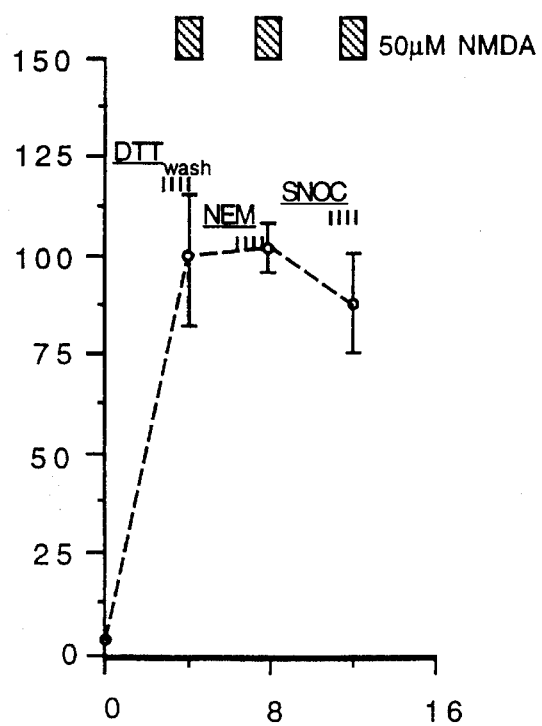

FIG. 5A–B are graph showing NMDA-evoked intracellular [Ca$^{2+}$] induced in cortical neurons and the effect of different redox agents including S-nitrosocysteine (SNOC). (See Example 5.)

FIG. 6A–D are bar graphs showing that sodium nitroprusside (SNP) or nitroglycerin (NTG) prevents NMDA-mediated neurotoxicity.

Figure 7A:
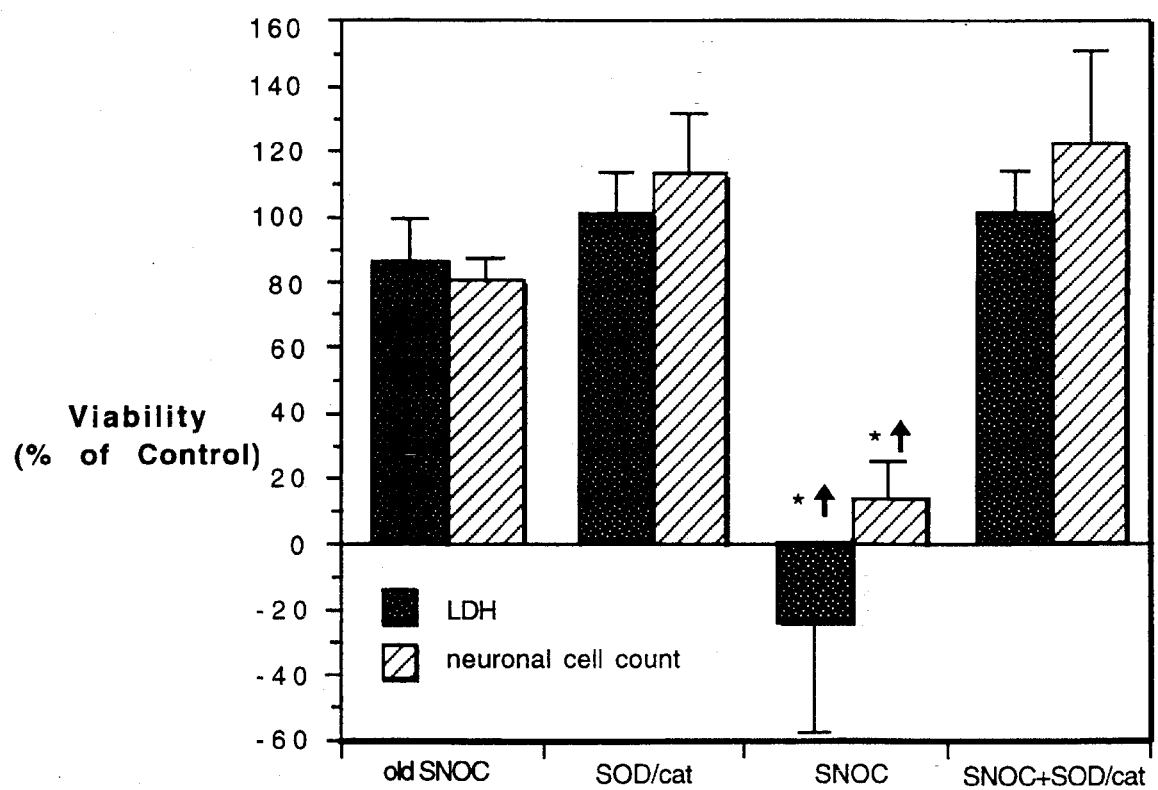
Figure 7B:
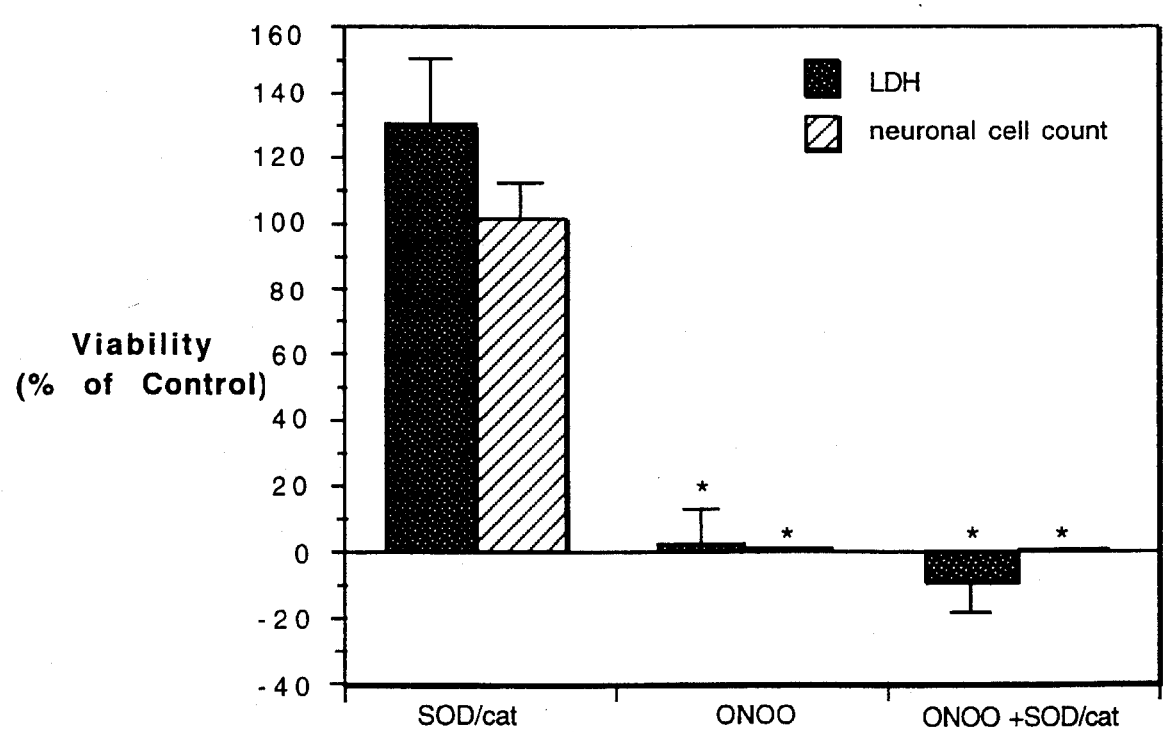

FIGS. 7A and 7B are bar graphs showing superoxide requirement of neurotoxicity induced by S-nitrosocysteine (SNOC) or peroxynitrite ($ONOO^-$).

The present invention is based on the finding that the compounds nitroprusside and nitroglycerin decrease NMDA receptor complex-mediated neuronal damage (see below).

This neuroprotection may be due to nitrosation or oxidation of the NMDA receptor at the redox modulatory site, resulting in NO group transfer to the thiol group(s) of the NMDA receptor's redox modulatory site to form an RS-NO ($NO^+$ equivalent). This chemical reaction leads to a decrease in NMDA receptor-operated channel activation by excitatory amino acids (such as NMDA or glutamate) and a concomitant decrease in intracellular calcium influx and amelioration of neurotoxicity.

An increased level or effect of one or more glutamate-related compounds is associated with many neurodegenerative disorders (e.g., those listed above). In addition to glutamate itself, neuronal injury may result from stimulation of the NMDA receptor-channel complex by other excitatory amino acids, such as aspartate, quinolinate, homocysteic acid, cysteine sulfonic acid, cysteine, or from stimulation by excitatory peptides, such as N-acetyl aspartyl glutamate.

Nitroglycerin (1,2,3-propanetriol trinitrate or glyceryl trinitrate, abbreviated NTG or GTN), sodium nitroprusside, and NO-generating derivatives of either one of those compounds are considered to be particularly useful in the invention.

Compounds of the second aspect of the invention (i.e., nitroso-compounds or NO-generating compounds and their derivatives) may be tested for efficacy in decreasing neuronal damage using the assays described below—i.e. in assays of NMDA-evoked ionic current (see, e.g., PCT WO 91/02810), in assays of NMDA- evoked increases in intracellular $Ca^{2+}$ (see below), or in assays of neuronal cell death (see below). An effective compound will cause a decrease in ionic current, intracellular $Ca^{2+}$ concentration, or in neuronal cell death, respectively. Compounds most preferred in the invention are those which effect the greatest protection of neurons from NMDA receptor complex-mediated injury, e.g., that injury resulting from stimulation of the NMDA receptor by NMDA(as shown below) or other excitatory amino acids or stimulation by excitatory peptides, such as N-acetyl aspartyl glutamate.

Assay for Neuronal Cell Function and Death

To test compounds for their ability to prevent neurotoxicity, neuronal cell death may be assayed as follows. Neonatal cortical neurons were prepared according to the general method of Snodgrass et al. (1980) Brain Res. 190:123–138; and Rosenberg et al (1988) J. Neurosci. 8:2887–2899. Cultures are monitored following a brief exposure (5–30 minutes) to 30–100 µM NMDA, or to 5 mM DTT (for 5 minutes) followed by 30–100 µM NMDA (for 5–30 additional minutes), and overnight incubation (i.e., 16 to 24 hours). Experiments in vivo suggest that a transient chemical reducing state exists in the brain following stroke; the introduction of the chemical reducing agent DTT may mimic this reducing environment, increasing the similarity of the in vitro assay to the in vivo situation. The candidate compound is tested by addition (e.g., in a series of concentrations ranging from 0.1 nM–10 mM) after DTT treatment but before NMDA treatment. The candidate compound can be added for minutes, hours, or even days prior to its washout period. Following NMDA exposure, the cultures are incubated an additional 16– 24 h at 37° C. in an atmosphere of 5% $CO_2$/95% air. Neuronal cultures are scored for cell survival after this overnight incubation because NMDA toxicity is often delayed by several hours following NMDA exposure. The ability of cortical neurons to maintain phase-bright appearance and exclude trypan blue is used as an index of survival (Rosenberg et al., *Neurosci. Lett.* 103: 162–168, 1989).

Measurement of Intracellular $Ca^{2+}$

The concentration of intracellular free $Ca^{2+}$ ($[Ca^{2+}]i$) is measured in neonatal cortical neurons by digital imaging microscopy with the $Ca^{2+}$ sensitive fluorescent dye fura 2, as follows. The same cortical neuronal cultures as described above are used. During $Ca^{2+}$ measurements, unless otherwise stated the fluid bathing the neurons consists of Hanks' balanced salts: 137.6 mM NaCl, 1 mM $NaHCO_3$, 0.34 mM $Na_2HPO_4$, 0.44 mM $KH_2PO_4$, 5.36 mM KCl, 1.25 mM $CaCl_2$, 0.5 mM $MgSO_4$, 0.5 mM $MgCl_2$, 5 mM Hepes NaOH, 22.2 mM glucose, and sometimes with phenol red indicator (0.001% v/v); pH 7.2. NMDA (in the absence $Mg^{++}$), glutamate, and other substances are usually applied to the neurons by pressure ejection after dilution in this bath solution. Neuronal $[Ca^{2+}]i$ is analyzed with fura 2-acetoxymethyl ester (AM) as described [Grynkiewicz, et al., *J. Biol. Chem.* 260:3440 (1985); Williams et al., *Nature* 318:558 (1985); Connor et al., J. Neurosci. 7:1384 (1987); Connor et al., *Science* 240:649 (1988); Cohan et al., *J. Neurosci.* 7:3588 (1987); Mattson, et al., ibid, 9:3728 (1989)]. After adding Eagle's minimum essential medium containing 10 µM fura 2-AM to the neurons, the cultures are incubated at 37° C. in a 5% $CO_2$/95% air humidified chamber and then rinsed. The dye is loaded, trapped, and deesterified within 1 hour, as determined by stable fluorescence ratios and the effect of the $Ca^{2+}$ ionophore ionomycin on $[Ca^{2+}]i$ is measured. During the $Ca^{2+}$ imaging, the cells are incubated in a solution of Hepes-buffered saline with Hanks' balanced salts. The $[Ca^{2+}]i$ is calculated from ratio images that are obtained by measuring the fluorescence at 500 nm that is excited by 350 and 380 nm light with a DAGE MTI 66 SIT or QUANTEX QX-100 Intensified CCD camera mounted on a Zeiss Axiovert 35 microscope. Exposure time for each picture is 500 ms. Analysis is performed with a Quantex (Sunnyvale, CA) QX7-210 image-processing system. Since cells are exposed to ultraviolet light only during data collection (generally less than a total of 20 s per cell), bleaching of fura 2 is minimal. Delayed NMDA-receptor mediated neurotoxicity has been shown to be associated with an early increase in intracellular $Ca^{2+}$ concentration.

Patch-Clamp Recording

Patch-clamp recordings were performed in the whole-cell configuration generally using the procedure described by Hamill et al. (1981) as modified by Lipton and Tauck (1987); and Aizenman et al. (1988). Patch-clamp pipettes typically contained 140 mM KCl (or 120 mM CsCl and 20 mM TEA-Cl), 2 mM $MgCl_2$, 2.25 mM EGTA, 10 mM HEPES-NaOH (pH 7.2). Redox reagents were administered by superfusion (3.5 ml/min), while NMDA and glycine were always coapplied by puffer pipette.

A compound may be tested for utility in the method of the invention using any type of neuronal cell from the central nervous system, as long as the cell can be isolated intact by conventional techniques. Although cortical neuron cultures are used above, retinal ganglion cell neurons, spinal cord neurons, cerebellar granular neurons, or any neuron containing NMDA receptors (e.g., neurons from other regions of the cortex) may also be used. Such neurons may be prenatal or postnatal.

The following examples illustrate compounds useful in the method of the invention and their efficacy in reducing neuronal damage. These examples are provided to illustrate the invention and should not be construed as limiting.

EXAMPLES 1–4

NTG or SNP Inhibits NMDA-Induced Increases in $[Ca^{++}]$ in Rat Cortical Neurons in Culture.

In this experiment, the effect of NTG on intracellular $[Ca^{++}]$ increases induced by NMDA were followed using digital [Ca$^{++}$] imaging techniques, based on the dye fura-2.

Specifically, the model for NMDA-mediated neurotoxicity involves exposure of cultured rat cortical neurons to NMDA in the presence of glycine (a co-agonist). NMDA (50 µM) induces an increase in [Ca++]$_i$ (intracellular calcium ion concentration) that is further enhanced after exposure to the strong reducing agent, dithiothreitol (DTT). Chemical reduction of the NMDA redox modulatory site thiol group(s) with DTT increases the neurotoxic effect of NMDA.

Antagonism of NMDA receptor-mediated neurotoxicity by NTG is demonstrated as follows.

Cortical cultures were derived from embryonic (fetal day 15 or 16) Sprague-Dawley rats as described previously (Dichter, 1978; Rosenberg and Aizenman, 1989). Briefly, following dissociation in 0.027% trypsin, cerebral cortical cells were plated at a density of 4.5×10$^5$ per 35 mm dish containing poly-L-lysine-coated glass coverslips in Dulbecco's modified Eagle's medium with Ham's F12 and heat-inactivated iron-supplemented calf serum (Hy-Clone) at a ratio of 8:1:1. After 15 days in culture (when the astrocyte layer had become confluent), the cultures were treated with cytosine arabinoside for 72 hr. The culture medium was replenished 3 times weekly. Cultures were incubated at 36° C. in a 5% $CO_2$, 95% air humified atmosphere. The cultures were used for experiments at room temperature (21° C.-24° C.) approximately 1 month after plating. Neurons could be reliably identified by morphological criteria under phase-contract optics, as later confirmed by patch-clamp recording.

To permit physiology experiments ($Ca^{2+}$ imaging or patch clamping) under normal room air conditions, just prior to a recording session the culture medium was exchanged for a solution based on Hanks' balanced salts (as defined above with 1.25–2.5 mM $CaCl_2$). To enhance physiological responses to NMDA, the saline was nominally $Mg^{2+}$ free and contained 1 µM glycine, a coagonist required for NMDA receptor activation (Johnson and Ascher, 1987; Kleckner and Dingledine, 1988). Tetrodotoxin (1 µM) was added to block action potentials and ensuing neurotransmitter release from other neurons onto the cell of interest. The presence of intact neurotransmission might have obfuscated the results if, for example, high K$^+$ kainate or NMDA caused the release of a substance from one neuron that in turn acted on the cell being monitored.

FIG. 1 shows quantifications of [Ca$^{2+}$]$_i$ from digital representations of fura-2 images over time for five cortical neurons in the field being imaged. DTT, NTG, DTNB (5,5-dithio-bis-2-nitrobenzoic acid) were applied (in that order) for approximately 2 minutes and washed out prior to data collection of NMDA-evoked [Ca$^{2+}$]$_i$ responses. These data were collected immediately following exposure to 50 µM NMDA.

In FIGS. 1 and 2, the NMDA-induced [Ca$^{2+}$]$_i$ response after DTT pretreatment was set at 100%. Prior to DTT pretreatment, the NMDA-induced [Ca$^{2+}$]$_i$ response was about 68%. Following DTT, subsequent NTG or SNP treatment decreased the NMDA-evoked [Ca$^{2+}$]$_i$ response to 60% or less. The strong oxidizing agent DTNB also decreased the NMDA evoked [Ca$^{2+}$]$_i$ responses. Subsequent treatment with DTT restored the NMDA-evoked [Ca$^{2+}$]$_i$ response to 100%.

EXAMPLE 2

Cortical cultures were prepared as described in Example 1 and were pretreated with DTT, washed, and treated with 100 µM NTG, followed by 50 µM NMDA. In FIG. 3, NTG persistently decreased the NMDA-evoked [Ca$^{2+}$]$_i$ response, and this decrease persisted through repeated readministration of NMDA. Readministration of DTT reversed the effect of NTG.

EXAMPLE 3

The cortical cultures described above were prepared as described in Examples 1 and 2, and patch clamp recordings were performed instead of digital Ca$^{2+}$ imaging. Specifically, NMDA (50 µM) was coapplied with glycine (1 µM) from a pneumatic pipette. Such application resulted in an inward current with the cell voltage clamped at a holding potential of −60 mV. A 2 min incubation in DTT (followed by washout) enhanced the NMDA-evoked current. This current was subsequently attenuated following a 2 min exposure to NTG (and washout). Reapplication of DTT (followed by washout) increased the current response to its previous value.

FIG. 4 illustrates sequential compilation of the peak NMDA-evoked currents for 18 cells following treatment (and subsequent washout) of each redox reagent listed on the abscissa. The temporal order of addition of the redox reagents is indicated on the abscissa. Values are mean ±SEM, normalized to the 50 µM NMDA response observed after exposure to DTT to permit comparison among several cells. Responses to NMDA that are statistically smaller than those previously obtained directly after DTT exposure are marked with an asterisk (P<0.001, ANOVA followed by Scheff+e,fra e+ee multiple comparison of means).

A 2 min exposure to DTT (2 mM, followed by washout) increased NMDA-activated currents, whereas the addition of NTG (500 µM, followed by washout) inhibited the responses. Subsequent incubation in DTNB (500 µM for 2 min, followed by washout) decreased the responses slightly.

EXAMPLE 4

The experiment of Example 3 was repeated using 1–5 mM NEM, N-ethylmalemide, an agent known to alkylate sulfhydryl (thiol) groups of proteins. Following alkylation, neither NTG nor DTNB significantly affected the amplitude of NMDA evoked current, indicating that the redox modulatory site of the NMDA receptor, the site reacting with the NO group, is comprised of a thiol group(s).

EXAMPLE 5

SNOC Decreases NMDA-Evoked [Ca$^2$]$_i$ Responses

S-nitrosocysteine (SNOC) both liberates NO. and participates in nitrosation (NO$^+$ equivalents reacting with protein thiol groups). FIG. 5A is a digital representation of fura-2 calcium images as described above, for 10 cortical neurons in a single field. Following each response to NMDA, Ca$^{2+}$]$_i$ returned to the baseline value within 1 min (data not shown for clarity). The data points are connected by dashed lines merely to emphasize the temporal order of addition. In each case, 2 mM DTT was applied for ~2 min and then washed out prior to the application of NMDA and data collection. Values are mean ±SEM, normalized to the NMDA (50 µM) response obtained after exposure to DTT (maximum response ~750 nM [Ca$^{2+}$]$_i$).

Following maximal chemical reduction with DTT, the NMDA-evoked response was increased, but was subsequently inhibited by a 3 min exposure to 100 µM S-nitrosocysteine (SNOC). Following washout of S-nitrosocysteine, the NMDA-elicited response recovered only slightly. A second exposure to DTT fully reversed the inhibitory effect of S-nitrosocysteine. Responses to NMDA that are statistically smaller than those obtained directly after DTT exposure are marked with an asterisk (P<0.01, ANOVA followed by Scheff+e,fra e+ee multiple comparison of means). FIG. 5B shows that pretreatment with NEM blocks the effect of SNOC by alkylating thiol group(s), thus preventing transnitrosation of the NO group to NMDA receptor thiol(s).

EXAMPLE 6

Nitroglycerin (NTG) or Sodium Nitroprusside (SNP) Prevents NMDA Receptor-Mediated Neurotoxicity Using the neurotoxicity assay described above, the compounds sodium nitroprusside and nitroglycerin were tested individually for their ability to increase survival of neonatal cortical neurons. The neuronal cells were incubated for 16–24 hours at 37° C. in a humidified atmosphere of 5% $CO_2$ and 95% air.

As shown in FIG. 6A–6D, surviving neurons are expressed as the percentage of viable neurons in the control culture dishes in the same experiment. The concentrations of drugs were as follows: APV (2 mM), NTG (100 μM), SNP (400 μM), DTT (0.5–2 mM), and reduced Hb (500 μM). In experiments with NTG, cultures were exposed to 30 μM NMDA for 30 min; for the SNP experiments, exposure was to 75 μM NMDA for 5 min. For the experiments with Hb, NTG or SNP was preincubated with a chemically reduced, purified preparation of Hb prior to addition to the cultures. Values are mean ± SEM for experiments run in triplicate on sibling cultures on separate days (total of 32 experiments). Astericks indicate significant difference compared with the value for DTT-NMDA exposure, P<0.05 (ANOVA followed by Scheffe multiple comparison of means.

Figure 6A:
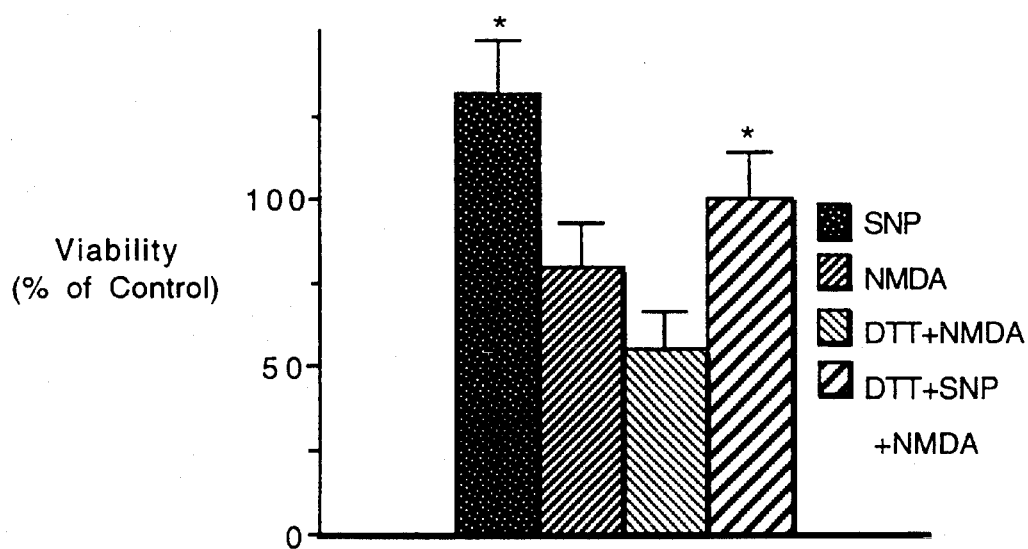
Figure 6B:
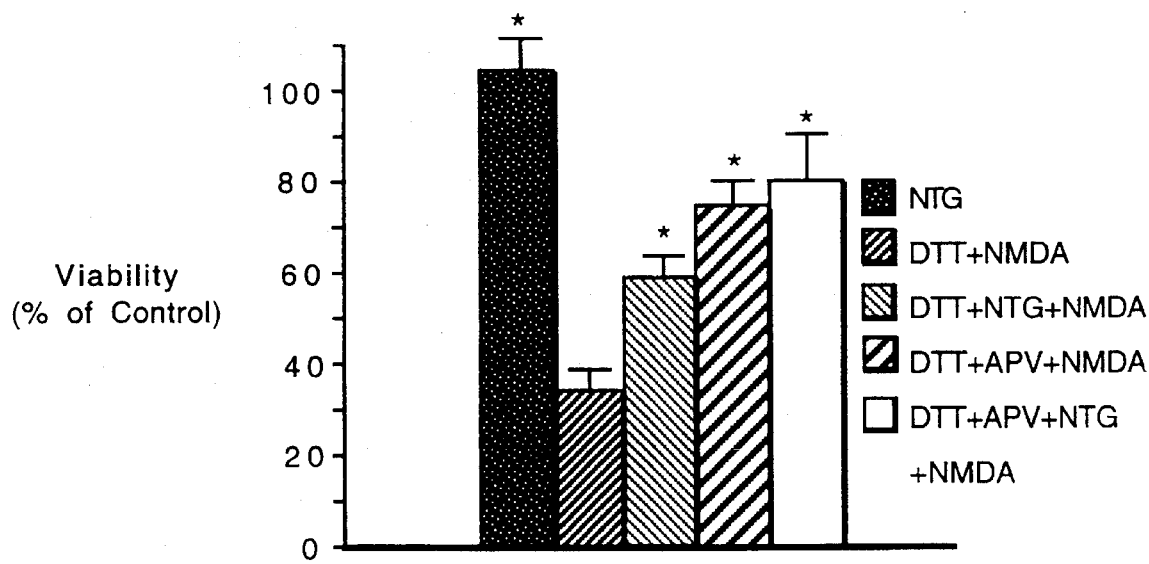
Figure 6C:
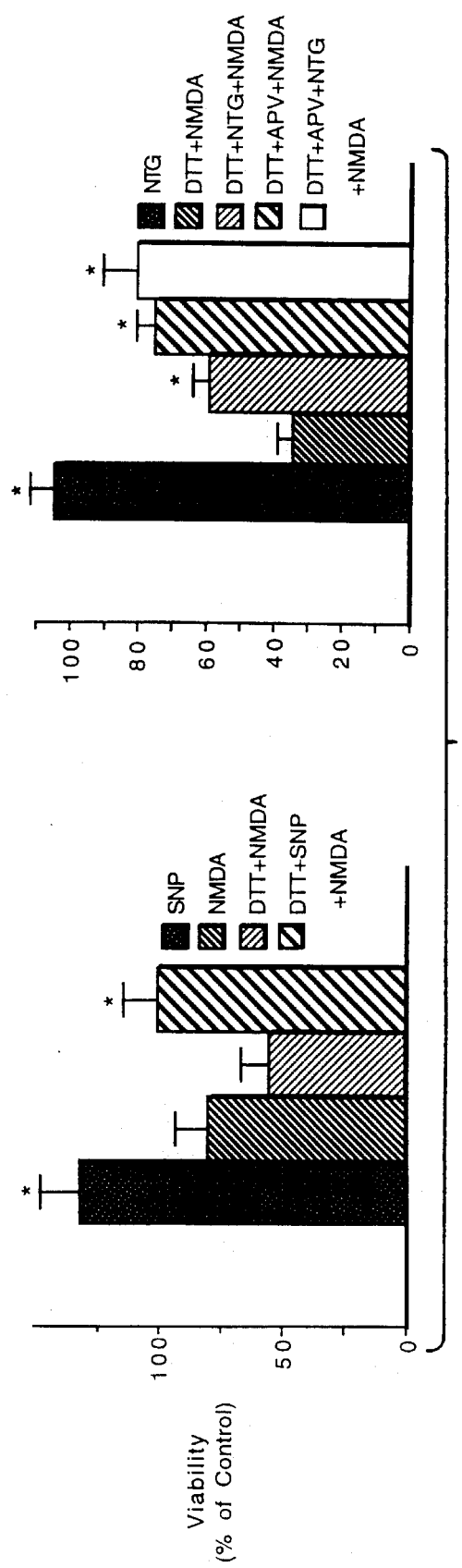
Figure 6D:
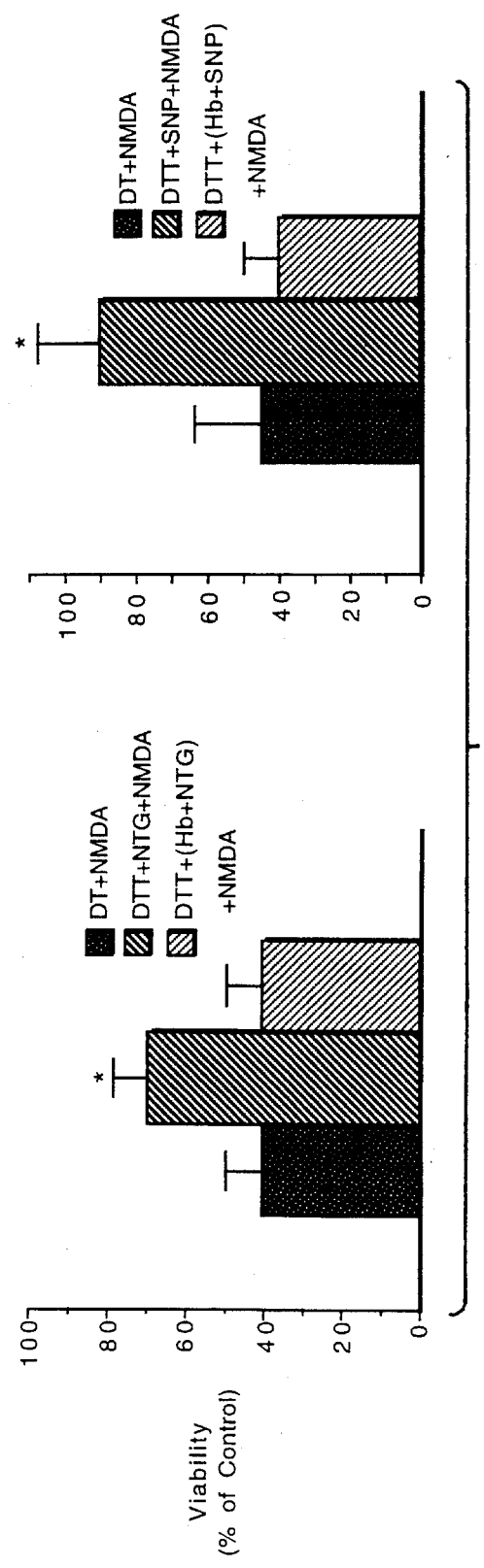

We found that either NTG or SNP ameliorated neuronal injury engendered by the addition of NMDA after exposure to DTT (FIGS. 6A and 6B). The latter compound was added to produce chemical reduction of the redox modulatory site in order to maximize NMDA-activated current, $[Ca^{2+}]_i$ responses, and neurotoxicity (as reported in the literature). The fact that a supramaximally effective concentration of the NMDA receptor-specific antagonist APV (2 mM) in combination with NTG failed to prevent neuronal cell death to a greater degree than APV alone suggests that the lethal effects were mediated via the NMDA receptor (FIG. 6B). In addition, exposure to 500 μM reduced hemoglobin (Hb), which complexes NO, did not affect neuronal survival on its own under these conditions; however, Hb completely inhibited the effect of 100 μM NTG, signifying that the protective action was mediated by NO (FIG. 6C). Reduced Hb (500 μM) also completely inhibited the protective action of 400 μM SNP, again suggesting the involvement of NO (FIG. 6D). It is likely that at least a part of the neuroprotective effect of NO is derived from oxidation of the redox modulatory site, since this action has previously been shown to attenuate NMDA receptor-mediated neurotoxicity.

EXAMPLE 7

Superoxide Dismutase (SOD) Plus Catalase Can Prevent Neurotoxicity Mediated by Peroxynitrite (ONOO–) formed from the Reaction of Nitric Oxide (NO.) with Superoxide Anion($O_{.2}^-$)

S-nitrosocysteine was added as a source of NO. to cerebrocortical cultures (Lei et al., (1992) Neuron 8:1087–1099; Stamler et al., (1992) Science 258:1898–1902). Incubation in this S-nitrosothiol (RS-NO) compound produced dose-dependent killing of cortical neurons. The neurotoxic effect of maximally-lethal concentrations of S-nitrosocysteine (200 μM) could be prevented by simultaneous addition of SOD and catalase (50 U/ml each) (FIG. 7A). These findings are consistent with the very rapid liberation of NO. ($t_{1/2(pH\ 7.4)}$) of S-nitrosocysteine ~30 s) for reaction with endogenous $O_2.^-$ to form peroxynitrite (ONOO–) with subsequent neuronal damage.

To test whether it is indeed peroxynitrite (and/or its decomposition products) that is neurotoxic, we next showed that purified OONO– kills neurons in a dose-dependent fashion. Peroxynitrite leads to lipid peroxidation and massive oxidation of sulfhydryls (Radi et al., (1991) J. Biol. Chem. 266:4244–4250; Radi et al., (1991) Arch. Biochem. Biophys. 288:481–487). In addition, as predicted if OONO– and/or its decomposition products were neurotoxic, reaction with SOD (Ischiropoulos et al., (1992) Arch. Biochem. Biophys. 298(2) :431–436) and catalase did not prevent the lethal action of peroxynitrite on neurons (FIG. 7B). These experiments indicate that SOD and catalase might be useful adjunctive neuroprotective agents that could be administered with the nitroso-compounds, such as NTG and SNP, in order to prevent NMDA receptor-mediated neurotoxicity, because SOD plus catalase would prevent the formation of neurotoxic ONOO– from any NO. that might be formed by the addition of the exogenous nitroso-compounds.

The results of the above experiments, as shown in FIG. 7, depict the superoxide anion requirement of neurotoxicity induced by S-nitrosocysteine (SNOC) but not peroxynitrite (ONOO–). A, B, Superoxide dismutase (SOD, 50 U/ml) plus catalase (cat, 50 U/ml) prevented neurotoxicity induced by SNOC (200 μM, B). Neuronal survival was not significantly affected in the presence of SOD/catalase alone compared to that observed in sibling control cultures. As an additional control, 200 μM SNOC that had been incubated at room temperature for several days, in order to release all NO species, did not result in neurotoxicity (A, far left columns, labeled "old SNOC"). Values are expressed as mean + s.e.m. (n=9). Statistical comparisons were performed by an analysis of variance followed by a Scheffe multiple comparison of means (*, P<0.01 compared to control; **, P <0.05 compared to control; †, P<0.01 compared to nitroso compound+ SOD/catalase).

Specifically, the data in FIG. 7 were generated using mixed neuronal and glial cortical cultures from neonatal rats, as described previously (Lei, et al., (1992) Neuron 8:1087–1099). In at least three separate experiments, triplicate cultures were incubated overnight in Earle's buffered saline solution (EBSS) containing various concentrations of SNOC, peroxynitrite, SOD, catalase, or glutamate. Similar results were obtained, however, with 20 min incubations in peroxynitrite, consistent with the known rapid effects of this potent oxidizing agent. The culture fluid was assayed for lactase dehydrogenase (LDH) as an indicator of neuronal survival by measuring the absorbance at 450 nm (Koh et al., (1987) J. Neurosci. Meth, 20:83–90). The cultures were also scored for neuronal viability by cell counting, generally with 0.2% trypan blue, after fixation in 2.5% glutaraldehyde, as described above. Neurons from cultures grown on 15 mm diameter cover slips were counted in a masked fashion in ~30 microscopic fields at 200x. Control cultures scored in this manner typically contained approximately 1000 viable neurons. Over the range of values illustrated here, there was a linear relationship between the neuronal cell counts and the LDH viability results, as determined by a standard curve based upon experiments with varying concentrations of glutamate (0–1 mM). For LDH assays, neuronal survival was normalized to that observed in control sibling cultures (100% viability value) and in the presence of 1 mM glutamate (0% viability value); values slightly below 0% were obtained by extrapolation but were not significantly different from 0%. Similar experiments on cultures of purified astrocytes (lacking neurons) did not produce changes in LDH.

Therapy

To prevent neuronal damage, compounds of the invention may be administered by any of a number of routes in an amount sufficient to attenuate an NMDA-evoked ionic current or a rise in $[Ca^{2+}]i$, or neurotoxicity. The compound may be included in a pharmaceutical preparation, using a pharmaceutical carrier (e.g., physiological saline); the exact formulation of the therapeutic mixture depends upon the route of administration. Preferably, the compound is administered orally or intravenously, but it may also be administered sublingually, by nasal spray, by transdermal patch, subcutaneously, intraventricularly, intravitreally, or by ointment. The preferred compounds, nitroglycerin or their derivatives (including all those preparations commercially available, e.g., those listed in the *Physician's Desk Reference* (1991) under coronary vasodilators or under nitroglycerin or nitroglycerin intravenous and including isosorbide mononitrate, isosorbide dinitrate, nitroglycerin sublingual, Minitran, NT-1, Niotrocor, Nitroderm, Nitrodisc, Nitro-dur, Nitro-Dur II, Nitrofilm, Nitrogard, Nitroglin, Nitropen, Tridil, and 6-chloro-2-pyridylmethyl nitrate) are administered at 0.01 mg–60 gm/day, in divided doses. Sodium nitroprusside— $Na_2[Fe(CN)_5NO]$—$2H_2O$ (from Elkins-Sinn, Inc., Cherry Hill N.J.), Nipride (from Roche, Nutley, N.J.), or other preparations—are administered intravenously at 0.5–10 μg/min.

Other nitroso-compounds, determined to be an effective neuroprotective agent by the assays described herein, are administered as above, at a dosage suitable to reduce neuronal damage, or NMDA evoked ionic current or increased $[Ca^{2+}]i$. Generally, such compounds are administered in dosages ranging from 0.01 mg–60 gm/day, more preferably in dosage of 0.1–5 mg/day.

Those skilled in the art will understand that there are other factors which aid in determining optimum dosage. For example, for NO-conjugated drugs, the dosage used for the unconjugated drug (e.g. TPA a dosage of 0.35–1.08 mg/kg and generally ≦0.85 mg/kg) is predictive of useful NO-conjugate dosage. Dosages may be divided. Treatment may be repeated as necessary to prevent or alleviate neurological injury. It is desirable to maintain levels of NO or related redox species in the brain of 1 nM to 500 μM.

For the CNS-protective purposes described herein, nitroso-compounds such as NTG and SNP can be administered acutely along with pressor agents (e.g., dopamine) to prevent a drop in systemic blood pressure.

With specific reference to nitroglycerin (NTG), I have also determined that patients can be made tolerant to the undesired systemic effects of NTG (e.g. blood pressure drop, coronary artery dilation or headache), without building tolerance to the desired neuroprotective effect of NTG, e.g., in the brain, spinal chord, and retina. Therefore, it is advantageous to induce NTG tolerance by gradually increasing dosage, thus increasing the neuronal protective effect.

To illustrate the development of systemic tolerance, a human patient could be made tolerant by intravenous administration of NTG within 18–24 hr of continuous infusion (see for example, J. E. Shaffer, B.-A. Han, W. H. Chern, and F. W. Lee, J. Pharmacol. Exper. Therap., 1992;260:286–293; D. C. May, J. J. Popma, Wh. H. Black, S. Scahaffer, H. R. Lee, B. D. Levine, and L. D. Hillis, New Engl. J. Med. 1987;317:805–809; C. M. Newman, J. B. Warren, G. W. Taylor, A. R. Boobis, and D. S. Davis, Br. J. Pharmacol. 1990;99:825– 829). Oral, nasal spray, or sublingual NTG could also be used to induce systemic tolerance.

Another, perhaps easier, method for making humans tolerant within 24 hours to the systemic effects of NTG is to administer nitroglycerin as nitropaste or as a transdermal patch for transdermal delivery, for instance, as follows: ½ inch every 4 to 6 hours, while monitoring the blood pressure (to see when hypotension subsides from the applied nitropaste). As tolerated (e.g., in the absence of sudden drops in blood pressure), the dose of nitropaste is increased to up to 3 inches with each administration. Under these conditions, tolerance (as evidenced by no effect on systemic blood pressure) will develop in 18–24 hours or less. Nevertheless, the therapeutic effect of NTG on the brain's NMDA receptors to prevent excitotoxicity should be maintained under these conditions.

An animal model demonstrating the above-described tolerance follows.

Rat pups were treated with nitroglycerin (NTG) approximately for 36–48 hours before performing bilateral carotid ligations. The dosing regimen for the 3 groups of rat pups used to generate the data was as follows.

Hair was removed from the abdominal region of the rat pup using a razor. One-quarter of a NTG patch (Minitran) was applied to the shaved area. A quarter patch of this size corresponds to a dose of 0.6 mg/24 hours (whole patch 2.4 mg/24 hr). Between 12 and 16 hours later, another quarter-patch was applied to the rat's abdomen, leaving the first on. This procedure was again repeated 12–16 hours later. Each rat pup received 3 or 4 quarter patches before surgery, which was performed two days later and consisted of bilateral carotid ligation followed by hypoxia to induce a stroke. Control animals did not receive NTG patches.

Using this procedure of inducing NTG systemic tolerance, the following results were obtained: In the control group, 7/11 (64%) of the animals suffered large (≧50%) cerebral cortical infarcts. In contrast, in the NTG-treated group, only 2/13 (15%) of the animals had any discernible cerebral infarct at all (P<0.03 by Fisher's exact test). Thus, NTG was cerebral protective when administered in this fashion.

In more recent trials, the ¼ patch that is first applied is taken off 12–16 hr later, and two new ¼ patches are applied. 12–16 hr later, the two quarter patches are removed, and 3 new (¼) patches are applied. This may be repeated using 4 new (¼)=1 whole patch. In this fashion, the dose may be escalated to 2, 3 or more whole patches.

Animals are operated on (to induce a stroke) approximately 48 hr after the initial administration of NTG patches.

To convert the dosage given to rat pups in these experiments to a human dose of a NTG patch, the following approximation was used. First, the rat weight in grams is converted to surface area in square meters and the dose of NTG is calculated as dose per square meter. In general, the rat pups used here weighed ~20 grams, equivalent to approximately $5 \times 10^{-3}$ square meters in surface area. Using a standard nomogram, the weight of a human (e.g., 60 kg) can be converted to square meters (~2 square meters for 60 kg). Thus, there is a scale factor in body area of 1:400 when converting rat to human dosage. In addition, the dose for a human per square meter would be approximately ¼ the dose per square meter given to a rat pup. Therefore, the human dose is approximately 100 times the rat dose, so that a patch containing 24 mg in the rat experiments is equivalent to a human patch containing about 240 mg. Such a human dose would have to be more slowly escalated to avoid initial hypotension with the first few NTG patch applications.

The compounds of the invention can be utilized to protect against a number of neurotoxic disorders associated with elevated levels or effects of glutamate or related compounds. Such disorders are mediated by stimulation of NMDA receptors or by downstream effects of NMDA receptor overstimulation. These disorders include ischemia, hypoxia, hypoglycemia, trauma to the nervous system, epilepsy, Huntington's disease, Alzheimer's disease, amyotrophic lateral sclerosis (ALS), Parkinson's disease, and other neurodegenerative disorders. Inherited or acquired chemical disorders mediated at least in part by NMDA receptor activation can also be treated. These include hyperammonemia, hepatic encephalopathy, hyperglycinemia, and others. See Tables 1 and 2. These include hyperammonemia, hepatic encephalopathy, hyperglycinemia and others (see Tables 1 and 2). Neuropathic pain syndromes such as causalgia may also be mediated in this manner and can be treated with the compounds of the invention. The method of the invention is particularly preferred for the treatment of the AIDS dementia complex (HIV-associated cognitive/motor complex plus incipient forms of cognitive, motor and sensory deficits not yet fulfilling the stringent criteria for these complexes) and other neurological manifestations of the AIDS virus (HIV-1 or HIV-2). The method may also be used for reduction of neuronal damage resulting from infection with other viruses, such as measles, which cause damage to the nervous system. Other diseases listed above can be treated.

One aspect of the invention features prolonged administration of increasing dosages of NO-generating compounds to establish tolerance of the vascular effects (coronary artery dilatation, blood pressure drop, etc.), thereby enabling higher dosages of the compounds for neuroprotection. One particular way to achieve this goal is to administer the NO-generating compound transdermally, using well established transdermal patch technology. Current transdermal nitroglycerin patches provide about 0.2–0.8 mg/hr. They have a typical surface area of 10–30 cm$^2$. The standard protocol for the use of such patches limits their use to about 12 continuous hours to avoid systemic tolerance.

In order to establish systemic tolerance and thereby increase the NO-generating levels available for neuroprotection, a patient is started on a regime of therapy similar to that currently used for cardiac conditions (e.g., patch loaded with about 2–4 mg nitroglycerin to be used for about 10 hours, or about 0.2–0.4 mg/hr). This regime is followed continuously, without any substantial (no more than 4–6 hours) hiatus. Gradually (e.g., after a day), the dosage is increased, and blood pressure is monitored to be sure that systemic tolerance has been achieved. The rate of increase will depend on the patient, but it generally will involve doubling the dosage every 24 hours for a period of 2–3 days. Typically, levels of about 3–4 mg/hr will be achieved, but dosage could go as high as 2.5 gm/hr. Dosage can be increased by increasing the loading of existing patches, by increasing the surface area of similarly loaded patches, or by increasing the efficiency of permeability and the frequency of readministration of the patches. Those skilled in the art will appreciate that there are many ways to achieve the goal of systemic tolerance. In one specific method, color coded patches can be used to reduce the chance for misuse (e.g., red, then white, then blue). The colors would signify the sequence of use of the respective patches. The final patches would be designed to administer levels of NTG that are higher than any currently available patch can administer. For example, the final patch may have a size of 50 cm$^2$ or more; or it may be loaded to deliver over 3mg/hr.

Those skilled in the art will appreciate that tolerance can also be achieved using slow release oral NTG (p.1166 of the 1992 PDR), or using ointments or other transdermal modalities.

Other Embodiments

The method described herein is useful for reducing neuronal injury in any mammal having NMDA receptors. Treatment of neuronal damage in humans is the preferred utility; but the method may also be employed successfully for veterinary purposes. The NO-generating compound may be co-administered with other redox compounds or enzymes to control superoxide ($O_2.^-$)-related damage. Nitric oxide (NO.) is known to react with $O_2.^-$ to form peroxynitrite (ONOO–) which we have shown is toxic to neurons (see FIG. 7, above). Superoxide dismutase (SOD) plus catalase decrease the $O_2.^-$ available for this reaction and therefore could enhance neuroprotection by allowing the NO reaction of nitrosation (transfer of NO$^+$equivalents to thiol groups) to predominate to provide protection by downregulating the NMDA receptor's redox modulatory site. SOD plus catalase, or similarly acting compounds, can be administered with polyethylene glycol to enhance their absorption into the CNS and efficacy (Liu et al., (1989) *Am. J. Physiol.* 256:589–593. An SOD mimic, the protein-bound polysaccharide of Coriolus versicolor QUEL, termed "PS-K", may also be effective by parenteral or oral routes of administration, especially with PEG to enhance CNS absorption. PQQ (pyrroloquinoline quinone-see U.S. Pat. No. 5,091,391, hereby incorporated by reference or PQQ's derivative esters or other quinones such as ubiquinone) could also be useful to accept an electron from NO. or from $O_2.^-$ to drive the reaction toward nitrosation with NO+ equivalent species and hence toward neuroprotection.

Similarly, other useful agents either by themselves or as adjunctive agents (to be administered with nitroso-compounds) would limit NO. production (e.g., nitric oxide synthase (NOS) inhibitors). Such treatment would avoid peroxynitrite (ONOO$^-$) formation and hence neuronal injury, e.g., contribution to the AIDS dementia complex and other neurological manifestations of AIDS. These agents are listed in Table 3 (enclosed).

TABLE 1

Acute Neurologic Disorders with Neuronal Damage Thought to be Mediated at Least in Part by Excitatory Amino Acids* i. domoic acid poisoning from contaminated mussels ii. cerebral ischemia, stroke iii. hypoxia, anoxia, carbon monoxide poisoning iv. hypoglycemia v. prolonged epileptic seizures vi. mechanical trauma to the nervous system vii. Pb (lead) poisoning

*For general reviews, see Choi, *Neuron* 1:623–34 (1988); and Meldrum and Garthwaite, *Trends Pharmacol. Sci.* 11: 379–387 (1990).

TABLE 2

Chronic Neurodegenerative Diseases with Neuronal Damage Thought or Proposed to be Mediated at Least in Part by Excitatory Amino Acids.* i. Neurolathyrism-BOAA (β-N-oxalylamino-L-alanine ) in chick peas ii. Guam Disease-BMAA (μ-N-methyl-amino-L-alanine) in flour from cycad seeds iii. Hungtington's disease iv. ALS (amyotrophic lateral sclerosis)

v. Parkinsonism vi. Alzheimer's disease vii. AIDS dementia complex (HIV-associated cognitive/motor complex)

viii. Olivopontocerebellar atrophy (some recessive forms associated with glutamate dehydrogenase deficiency)

ix. Hepatic encephalopathy x. Tourette's syndrome xi. Mitochondrial abnormalities and other inherited biochemical disorders
   a. MELAS syndrome (mitochondrial myopathy, encephalopathy, lactic acidosis and stroke-like episodes)
   b. Rett syndrome
   c. homocysteinuria
   d. hyperprolinemia
   e. hyperglycinemia
   f. hydroxybutyric aminoaciduria
   g. sulfite oxidase deficiency

*For general reviews, see Choi, Neuron 1:623–34 (1988); and Meldrum and Garthwaite, Trends Pharmacol. Sci. 11:379–387 (1990).

TABLE 3

Nitric Oxide Synthase Inhibitors:

1. Arginine analogs including N-mono-methyl-L-arginine (NMA)
2. N-amino-L-arginine (NAA)
3. N-nitro-L-arginine (NNA)
4. N-nitro-L-arginine methyl ester
5. N-iminoethyl-L-ornithine
6. Diphenylene iodonium and analogs See, Steuhr, FASEB J 5:98–103 (1991)
7. Diphenyliodonium, calmodulin inhibitors such as trifluoparizine, calmidazolium chloride
8. Phospholipase $A_2$ inhibitors such as aristolochic acid
9. Calcineurin inhibitors, e.g., FK-506, cyclosporin A, and analogs including rapamycin (inhibit calcineurin and thus nitric oxide synthase by inhibiting its dephosphorylation)

I claim:

1. A method of administering nitroglycerin to a patient in need thereof to protect against neuronal degeneration, said method comprising administering nitroglycerin over time at escalating dosages to establish tolerance to blood pressure reduction caused by nitroglycerin, and, thereafter, administering a neuroprotective dosage of nitroglycerin, high enough to reduce blood pressure in a naive individual, whereby the patient's blood pressure is reduced less by said neuroprotective dosage than the blood pressure reduction experienced by a naive individual receiving said neuroprotective dosage.

2. The method of claim 1 wherein said neuronal degeneration is incident to ischemia.

3. The method of claim 1 wherein said neuronal degeneration is incident to stroke or cardiovascular disease.

4. The method of claim 1 wherein said nitroglycerin is administered in multiple progressively higher dosages until said neuroprotective dosage is achieved, and then said nitroglycerin is administered multiple times at said neuroprotective dosage level.

5. The method of claim 1 wherein said nitroglycerin is administered orally.

6. The method of claim 1 wherein said nitroglycerin is administered by transdermal patch.

7. The method of claim 1 wherein said nitroglycerin is administered at said neuroprotective dosage level by a patch having a surface area exceeding 50 $cm^2$.

8. The method of claim 1 wherein said nitroglycerin is administered at said neuroprotective dosage level by a patch loaded to deliver more than 3.0 mg/hr.

9. The method of claim 1 wherein said nitroglycerin is administered at said neuroprotective dosage level by a patch containing at least 30 mg of nitroglycerin.

10. The method of claim 1 wherein said nitroglycerin is administered to said patient continuously for a period exceeding 12 hours.

11. The method of claim 10 wherein said nitoglycerin is administered to said patient continuously for a period exceeding 24 hours.

* * * * *

UNITED STATES PATENT AND TRADEMARK OFFICE
CERTIFICATE OF CORRECTION

PATENT NO. : 5,455,279
DATED : October 3, 1995
INVENTOR(S) : Stuart A. Lipton

It is certified that error appears in the above-indentified patent and that said Letters Patent is hereby corrected as shown below:

On the title page:

In the references cited section, the "Choi" reference is duplicated;

In the abstract, "$NO^{31}$" should be --$NO^-$--;

Col. 1, line 62, "$NO^-$" should be --$NO\cdot$--;

Col. 1, line 66, "NO." should be --$NO\cdot$--;

Col. 1, line 66, "$NO^{31}$" should be --$NO^-$--;

Col. 3, line 26, "e-lipoic" should be --α-lipoic--;

Col. 3, lines 29-30, the footnote should be moved to the end of the column;

Col. 3, line 43, "NO," should be --$NO\cdot$--;

Col. 3, line 56, "NO." should be --$NO\cdot$--;

Col. 4, line 26, "NO." should be --$NO\cdot$--;

UNITED STATES PATENT AND TRADEMARK OFFICE
CERTIFICATE OF CORRECTION

PATENT NO. : 5,455,279
DATED : October 3, 1995
INVENTOR(S) : Stuart A. Lipton

It is certified that error appears in the above-indentified patent and that said Letters Patent is hereby corrected as shown below:

Col. 4, line 47, after "Drawings" start a new paragraph;

Col. 8, line 29, "Scheff+e,fra e+ee" should be --Scheffé--;

Col. 8, line 48, "NO." should be --NO·--;

Col. 9, line 3, "Scheff+e,fra e+ee" should be --Scheffé--;

Col. 9, line 59, "NO." should be --NO·--;

Col. 9, line 61, "NO." should be --NO·--;

Col. 10, line 2, "NO." should be --NO·--;

Col. 10, line 22, "NO." should be --NO·--;

Col. 14, line 10, "NO." should be --NO·--;

UNITED STATES PATENT AND TRADEMARK OFFICE
CERTIFICATE OF CORRECTION

PATENT NO. : 5,455,279
DATED : October 3, 1995
INVENTOR(S) : Stuart A. Lipton

It is certified that error appears in the above-indentified patent and that said Letters Patent is hereby corrected as shown below:

Col. 14, line 28, "NO." should be --NO·--;

Col. 14, line 33, "NO." should be --NO·--;

Col. 14, line 62, "$\mu$" should be --$\beta$--;

Signed and Sealed this

Fourteenth Day of January, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO.    : 5,455,279
DATED         : OCTOBER 3, 1995
INVENTOR(S)   : STUART A. LIPTON

It is certified that error appears in the above-identified patent and that said Letters Patent is hereby corrected as shown below:

At column 1, line 5, before "BACKGROUND OF THE INVENTION" insert --This invention was made with government support under Grant No. R01 EY05477 by the NIH. The government has certain rights in the invention.--

Signed and Sealed this

Twenty-sixth Day of September, 2000

Attest:

Q. TODD DICKINSON

*Attesting Officer*    *Director of Patents and Trademarks*